(12) United States Patent
Satasiya et al.

(10) Patent No.: US 8,439,934 B2
(45) Date of Patent: May 14, 2013

(54) MEDICAL DELIVERY DEVICE WITH A PROTECTIVE MEMBER

(75) Inventors: Pankaj Satasiya, San Jose, CA (US);
William Webb, Huntersville, NC (US);
Jason Reynolds, Barnegat, NJ (US);
Robert R. Snider, Dallas, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 791 days.

(21) Appl. No.: 12/535,980

(22) Filed: Aug. 5, 2009

(65) Prior Publication Data

US 2010/0049295 A1 Feb. 25, 2010

Related U.S. Application Data

(60) Provisional application No. 61/090,139, filed on Aug. 19, 2008.

(51) Int. Cl.
*A61F 2/95* (2006.01)
(52) U.S. Cl.
USPC .......................................... 606/108; 623/1.12
(58) Field of Classification Search .................. 606/108, 606/191, 192, 194, 198; 623/1.11, 1.12
See application file for complete search history.

(56) References Cited

U.S. PATENT DOCUMENTS

| | | | |
|---|---|---|---|
| 5,201,757 A | 4/1993 | Heyn et al. |
| 5,759,186 A | 6/1998 | Bachmann et al. |
| 5,824,041 A | 10/1998 | Lenker et al. |
| 5,868,755 A | 2/1999 | Kanner et al. |
| 5,954,729 A | 9/1999 | Bachmann et al. |
| 6,143,021 A | 11/2000 | Staehle |
| 6,162,231 A | 12/2000 | Mikus et al. |
| 6,391,051 B2 | 5/2002 | Sullivan, III et al. |
| 6,413,269 B1 | 7/2002 | Bui et al. |
| 6,428,566 B1 | 8/2002 | Holt |
| 6,514,261 B1 | 2/2003 | Randall et al. |
| 6,669,719 B2 | 12/2003 | Wallace et al. |
| 6,726,712 B1 | 4/2004 | Raeder-Devens et al. |
| 6,866,669 B2 | 3/2005 | Buzzard et al. |
| 7,731,654 B2 | 6/2010 | Mangiardi et al. |
| 2002/0151967 A1 | 10/2002 | Mikus et al. |

(Continued)

FOREIGN PATENT DOCUMENTS

| | | |
|---|---|---|
| DE | 43 23 866 A1 | 1/1994 |
| EP | 0 364 420 A | 4/1990 |

(Continued)

OTHER PUBLICATIONS

Office Action for U.S. Appl. No. 10/585,430 dated Nov. 9, 2010.

(Continued)

*Primary Examiner* — Brian E. Pellegrino
(74) *Attorney, Agent, or Firm* — Stoel Rives LLP

(57) ABSTRACT

A delivery device for positioning and deploying an implantable device within a lumen is provided. The delivery device includes inner and outer tubular members slidable to each other between at least a first hold position and a second release position, a handle and a deployment mechanism adapted for an operator to use a first hand for operating the delivery device and moving the tubular members between the first and second positions. The delivery device further includes a protective member adapted for insulating at least a portion of the outer tubular member from the tendency of the operator to use his or her second hand to grab the outer tubular member during operations or from other external forces.

19 Claims, 10 Drawing Sheets

U.S. PATENT DOCUMENTS

| | | |
|---|---|---|
| 2002/0183827 A1 | 12/2002 | Derus et al. |
| 2003/0050686 A1 | 3/2003 | Raeder-Devens et al. |
| 2003/0167060 A1 | 9/2003 | Buzzard et al. |
| 2004/0193243 A1 | 9/2004 | Mangiardi et al. |
| 2004/0267281 A1 | 12/2004 | Harari et al. |
| 2005/0090887 A1 | 4/2005 | Pryor |
| 2005/0125050 A1 | 6/2005 | Carter et al. |
| 2005/0149160 A1 | 7/2005 | McFerran |
| 2005/0278010 A1 | 12/2005 | Richardson |
| 2007/0043421 A1 | 2/2007 | Mangiardi et al. |
| 2007/0100421 A1 | 5/2007 | Griffin |
| 2007/0208350 A1 | 9/2007 | Gunderson |
| 2009/0118740 A1 | 5/2009 | Mangiardi et al. |
| 2010/0049295 A1 | 2/2010 | Satasiya et al. |

FOREIGN PATENT DOCUMENTS

| | | |
|---|---|---|
| EP | 0 872 220 A1 | 10/1998 |
| WO | WO 96/31174 | 10/1996 |
| WO | WO-00/78246 A2 | 12/2000 |
| WO | WO 02/087470 | 11/2002 |
| WO | WO 03/090644 | 11/2003 |
| WO | WO 2004/030571 | 4/2004 |
| WO | WO 2005/070095 | 8/2005 |
| WO | WO 2008/042266 | 4/2008 |

OTHER PUBLICATIONS

Office Action dated Jun. 7, 2011 for U.S. Appl. No. 10/585,430.
PCT Notification of Transmittal of the International Search Report and the Written Opinion of the International Searching Authority, or the Declaration, mailed Aug. 28, 2006 for PCT/US2006/018811 (Filed May 12, 2006).
The Supplementary European Search Report for EP Application No. 05705271.4, dated May 4, 2007.
International Search Report and Written Opinion for PCT/US2009/052691 dated Oct. 29, 2009.
Office Action for U.S. Appl. No. 11/432,964 dated Jul. 9, 2009.
Office Action for U.S. Appl. No. 11/432,964 dated Dec. 7, 2009.
International Search Report and Written Opinion for PCT/US05/00515 dated Sep. 28, 2005.
Office Action for U.S. Appl. No. 10/585,430 dated Dec. 8, 2009.
International Search Report from International Application No. PCT/US2009/052691, filed Aug. 4, 2009.
Office Action for U.S. Appl. No. 10/585,430 dated Aug. 13, 2012.
Office Action dated Jan. 31, 2012 for U.S. Appl. No. 10/585,430.
Office Action dated Jan. 22, 2013 for U.S. Appl. No. 10/585,430.

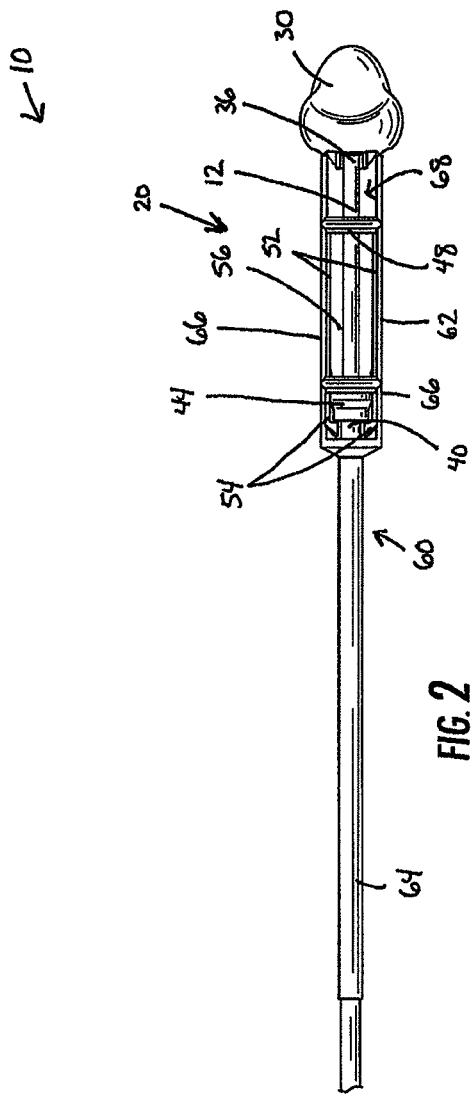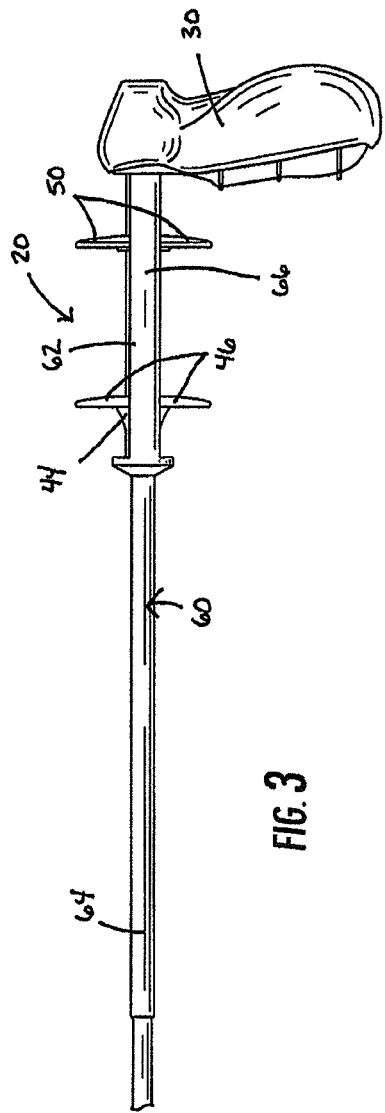

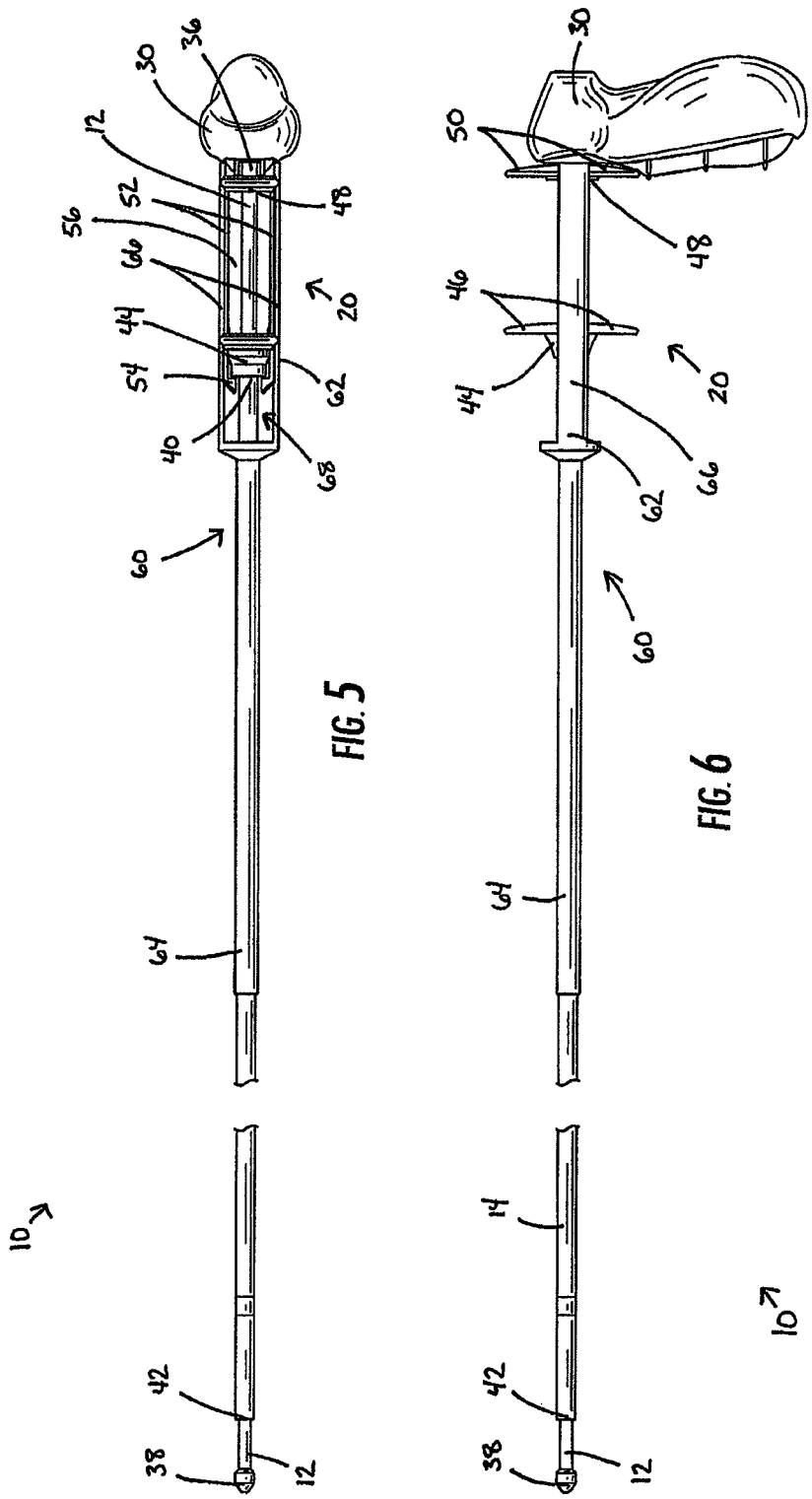

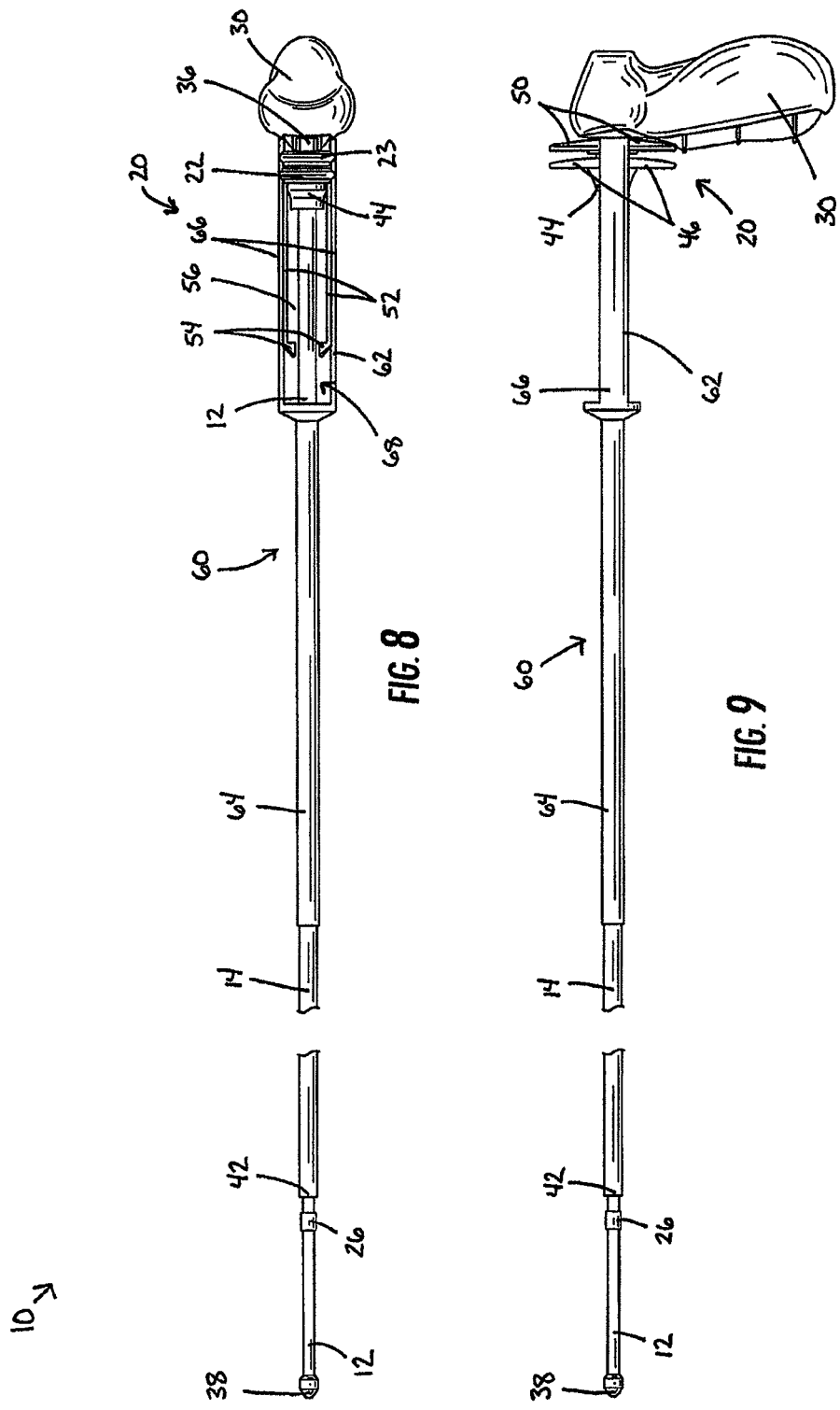

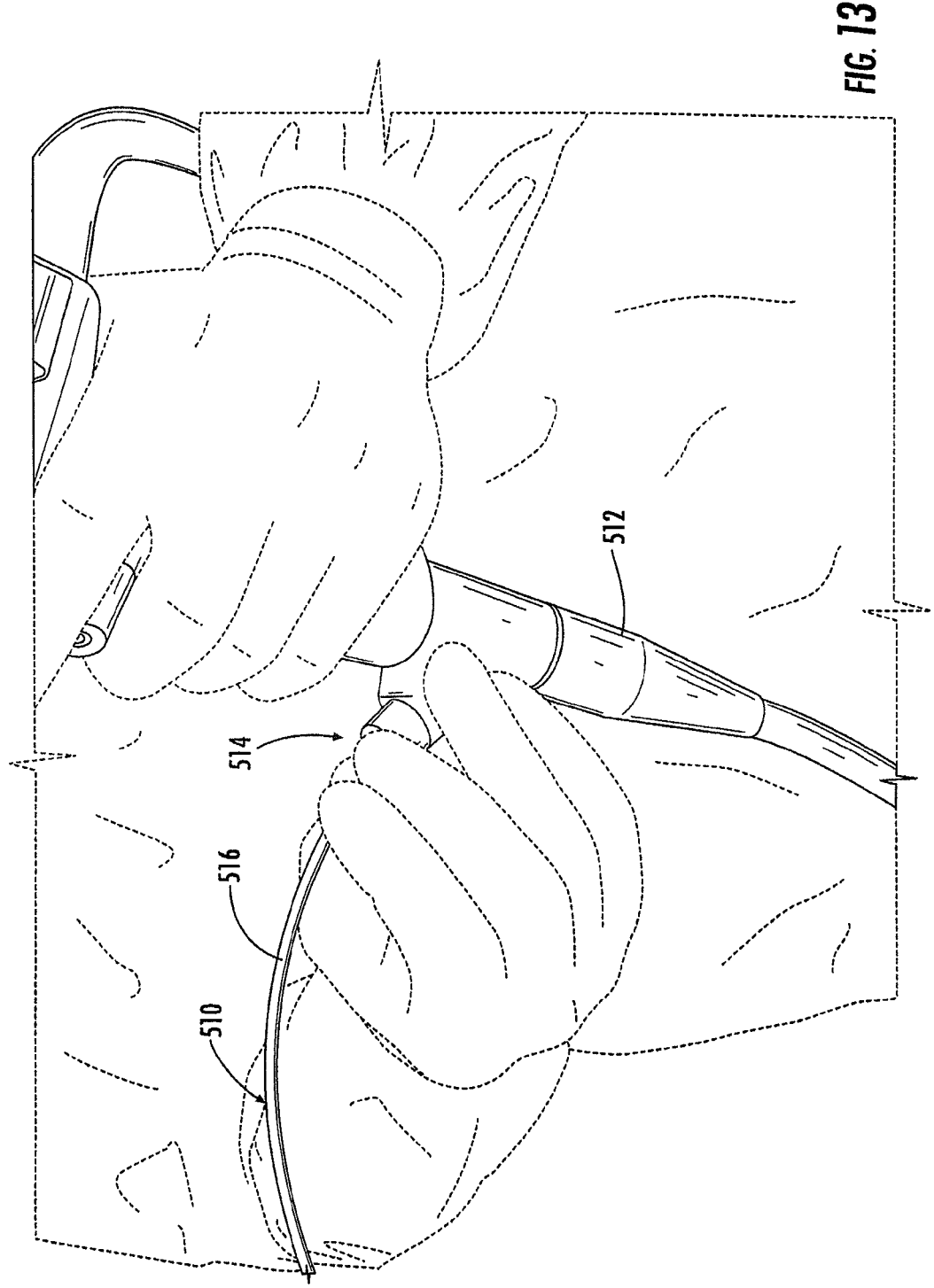

MEDICAL DELIVERY DEVICE WITH A PROTECTIVE MEMBER

CROSS REFERENCE TO RELATED APPLICATIONS

This application claims the benefit of U.S. Provisional Application No. 61/090,139, filed Aug. 19, 2008, which is incorporated by reference herein in its entirety.

BACKGROUND OF THE INVENTION

1) Field of the Invention

The present invention relates to a delivery device and to a delivery device for positioning and deploying an implantable device within a lumen.

2) Description of Related Art

Implantable medical devices are valuable tools of modern medicine. In general, an implantable device is a device or structure configured to be inserted or embedded into a patient for a variety of functions. Implantable devices include stents, filters, markers, drug delivery devices, valves, and monitors.

In particular, stents are implantable devices that are inserted into body lumina such as vessels or passages to keep the lumen open and prevent closure due to a stricture, external compression, or internal obstruction. Stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer. Vascular as well as nonvascular stenting has evolved significantly; unfortunately, there remain significant limitations with respect to effectively implanting the stents into a patient's lumen.

In order to serve its desired function, the stent and most other implantable devices must be delivered precisely and oriented correctly. Improper installation can lead to several adverse complications including tissue luminal inflammation and tissue granulation. In order to facilitate the delivery of implantable devices, delivery devices, such as endoscopes and catheters, have been utilized to deploy implantable devices more precisely.

Delivery devices vary in shape and structure. However, in general, a delivery device includes a handle and one or more movable tubular members extending from the handle. The delivery device further includes a deployment mechanism for moving or operating the tubular members between positions. For example, International Publication Number WO 2005/070095 to Mangiardi et al., which is assigned to the assignee of the present application and is incorporated herein by reference, discloses a delivery device having a handle, a deployment mechanism, and an inner tubular member disposed within an outer tubular member. The outer tubular member is typically shorter than the inner tubular member and movable relative to the inner tubular member. A distal region of the outer tubular member surrounds the implantable device, such as a stent, and maintains the stent in a crimped delivery configuration, while a distal region of the inner tubular member is surrounded by the stent. Once properly positioned at a targeted site, the outer tubular member is retracted to deploy the stent and allow the stent to radially expand.

The effective release of the stent depends on the movement of the outer tubular member relative to the inner tubular member. Therefore, an impairment of the movement between the tubular members may adversely affect the accuracy of the stent release. Although the sources of such impairment may vary, one known source is the operator of the delivery device. More specifically, some operators have a tendency to grasp the outer tubular member during use of the delivery device, which may impair the movement between the tubular members. As another example, the tubular members may become pinched or otherwise interfered with due to the tortuous path that the delivery device may take within the patient's lumen or from the pressure of the walls of the patient's lumen.

In light of the foregoing, there is a need in the industry for a delivery device with enhanced protection for the tubular members.

BRIEF SUMMARY OF THE INVENTION

The invention addresses the above needs and achieves other advantages by providing a delivery device for deploying an implantable device within a lumen. The inventive delivery device includes a protective member for insulating at least a portion of the outer tube from external forces, such as an operator's hand or from the patient's lumen. Insulating any portion of the outer tube from external forces reduces the likelihood of the outer tube being pinched and interfering with the movement between the inner and outer tubes and thus the accurate deployment of the implantable device.

In particular, according to an embodiment of the present invention, the delivery device includes a first elongate member having a proximal end and a distal end and a second elongate member having a proximal end and a distal end. The first and second members are configured to cooperatively retain an implantable device near the distal ends and to move relative to each other to release the implantable device into the lumen. The delivery device further includes a protective member configured to extend over at least one portion of the elongate members wherein relative movement occurs and to inhibit impingement of external forces on the relative movement of the at least one portion of the elongate members.

The first elongate member may include an outer tubular member and the second elongate member may include an inner tubular member. The inner tubular member may extend slidably within the outer tubular member. And the inner and outer tubular member may define a space near and between their respective distal ends to retain the implantable device.

The protective member may include a protective tubular member extending over a proximal portion of the inner and outer tubular members where gripping is likely to occur.

The delivery device may further include a handle and a deployment mechanism. The handle may be coupled to the inner tubular member, the outer tubular member, or both. The deployment mechanism may also be coupled to the inner tubular member, the outer tubular member, or both. Furthermore, the deployment mechanism is operable to deploy the implantable device within the lumen. The protective member may extend along at least a portion of the outer tubular member from either the handle or deployment mechanism toward the distal end of the outer tubular member.

The handle may be coupled to the proximal end of the inner tubular member and the deployment mechanism may include one or more actuators. At least one actuator is coupled to the proximal end of the outer tubular member. Also, each actuator has one or more flanges. For example, the delivery device may have two actuators and each actuator may have two flanges. The second actuator may have two more connector arms for operatively coupling the second actuator to the first actuator.

The protective member may include a proximal region and a distal region extending from approximately the handle to distally beyond the deployment mechanism and toward the distal end of the outer tubular member. The proximal region may define one or more grooves in which the flanges of the actuators are slidable within. For example, the proximal region may have two grooves. The distal region may extend along and around at least a portion of the outer tubular member. And the outer tubular member may be slidable within the distal region. The distal region may define a sheath having a substantially solid tubular wall or define a tubular wall having one or more apertures. The protective member may be formed from a variety of materials including polypropylene, polyvinyl chloride, and polyethylene.

According to another embodiment of the present invention, the handle and the deployment mechanism are adapted to be operated by a first hand of an operator for moving the outer and inner outer tubular members between at least a first position and a second position, and the protective member is adapted to be grasped by a second hand of the operator independently from the moving of the outer and inner tubular members between the at least first and second positions.

BRIEF DESCRIPTION OF THE SEVERAL VIEWS OF THE DRAWINGS

Figure 1:
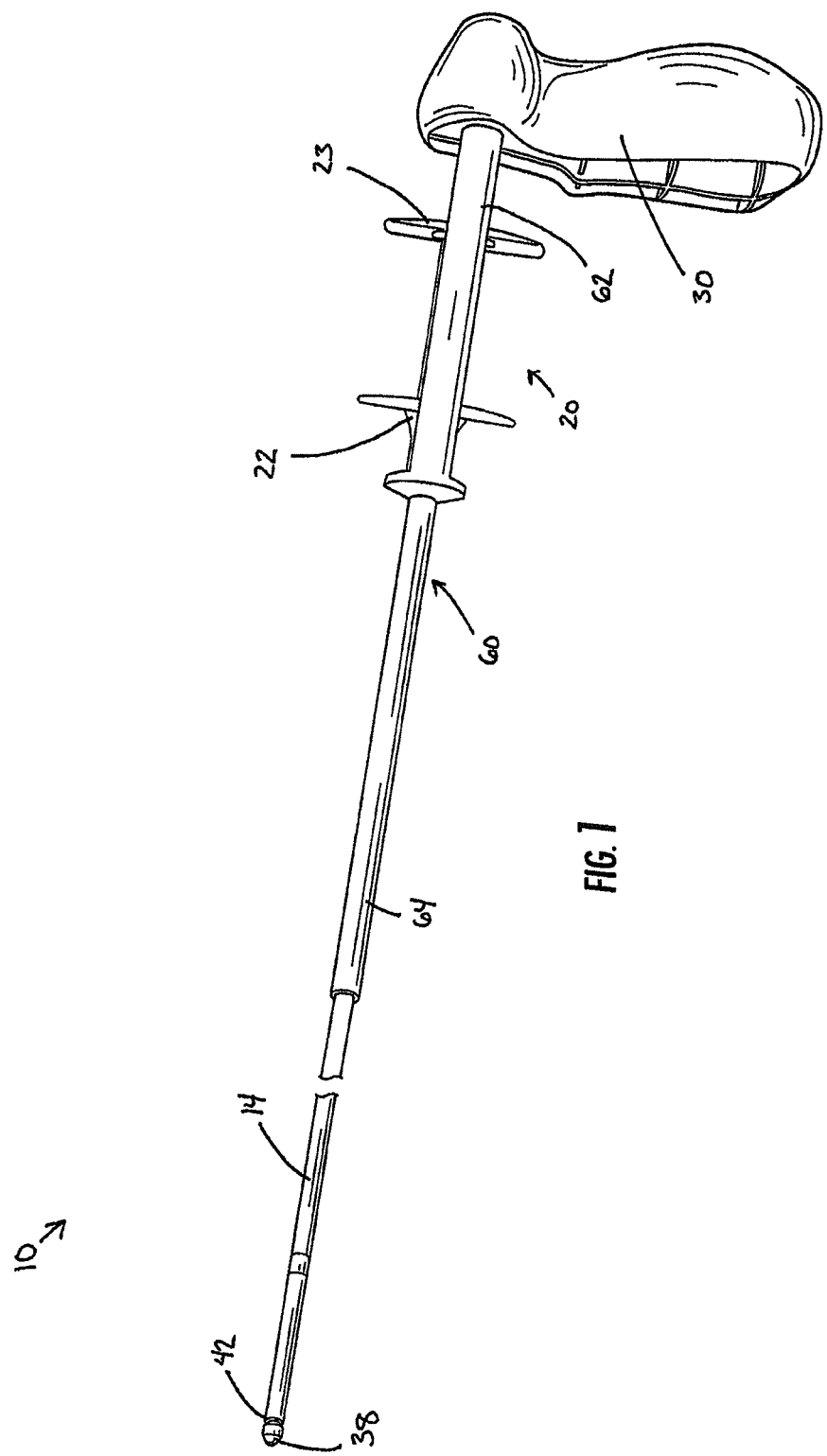
Figure 4:
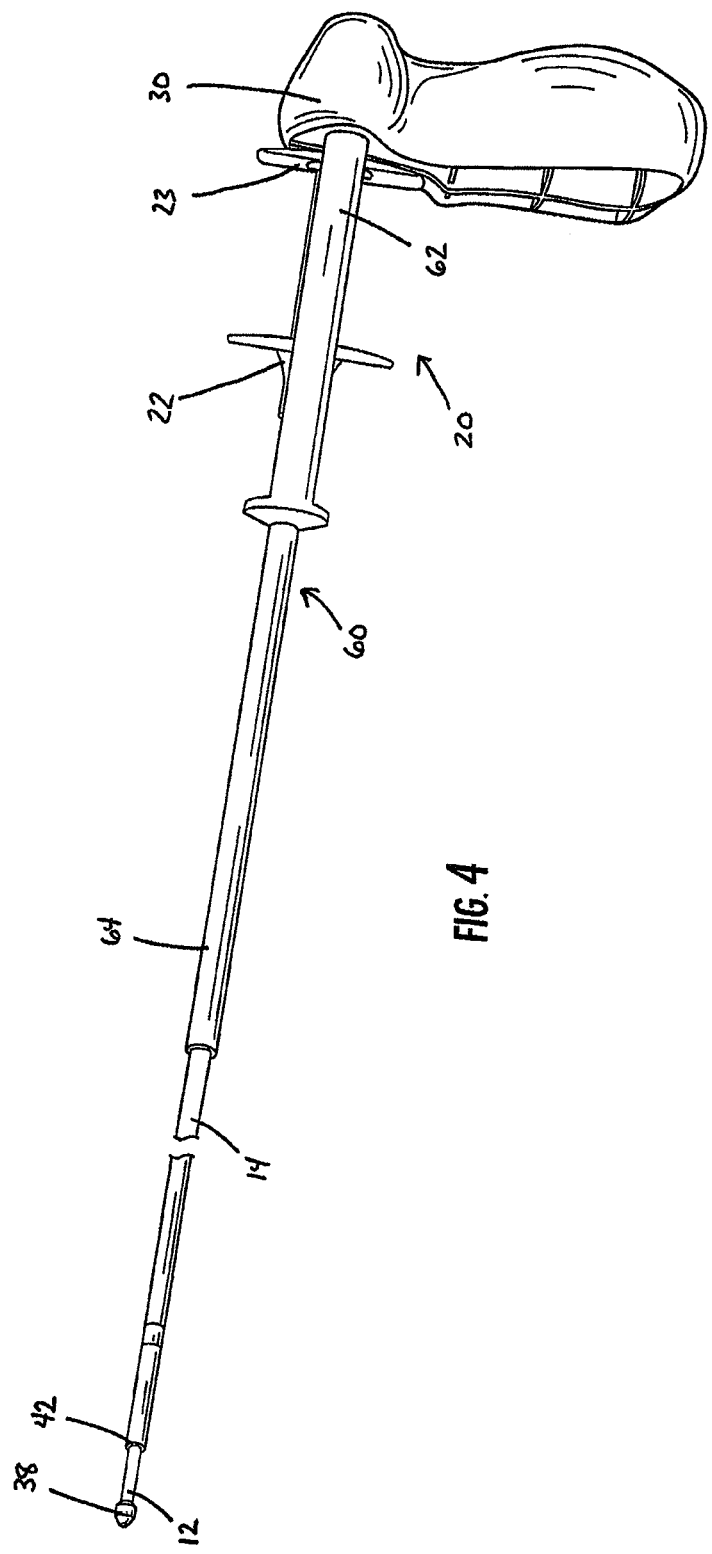
Figure 7:
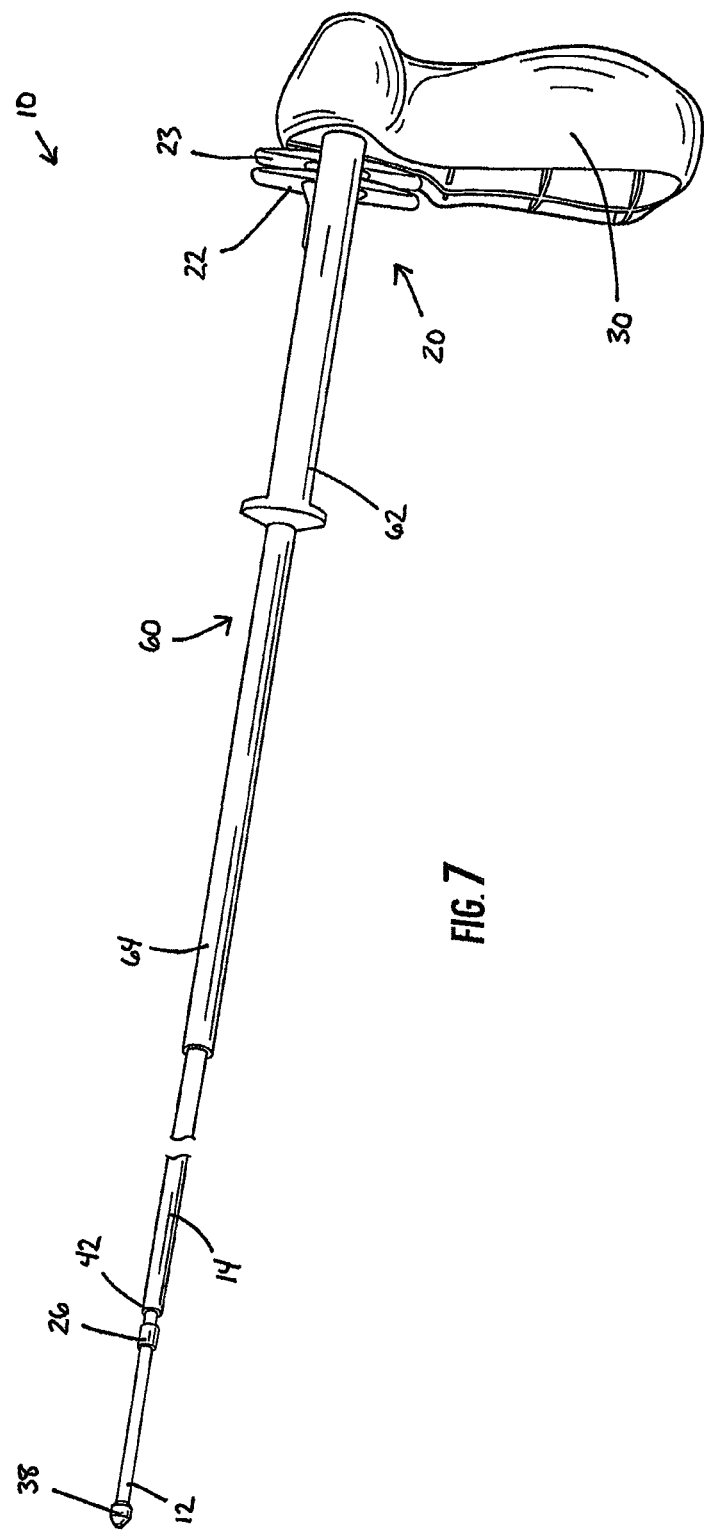
Figure 10:
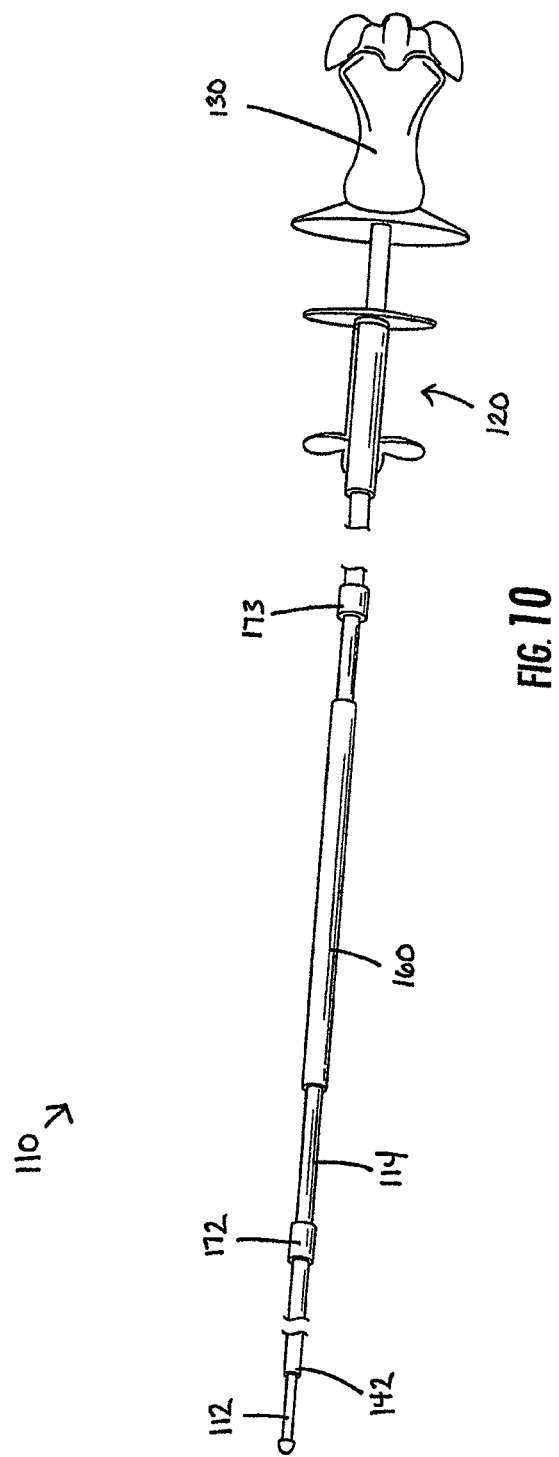
Figures 11A, 11B:
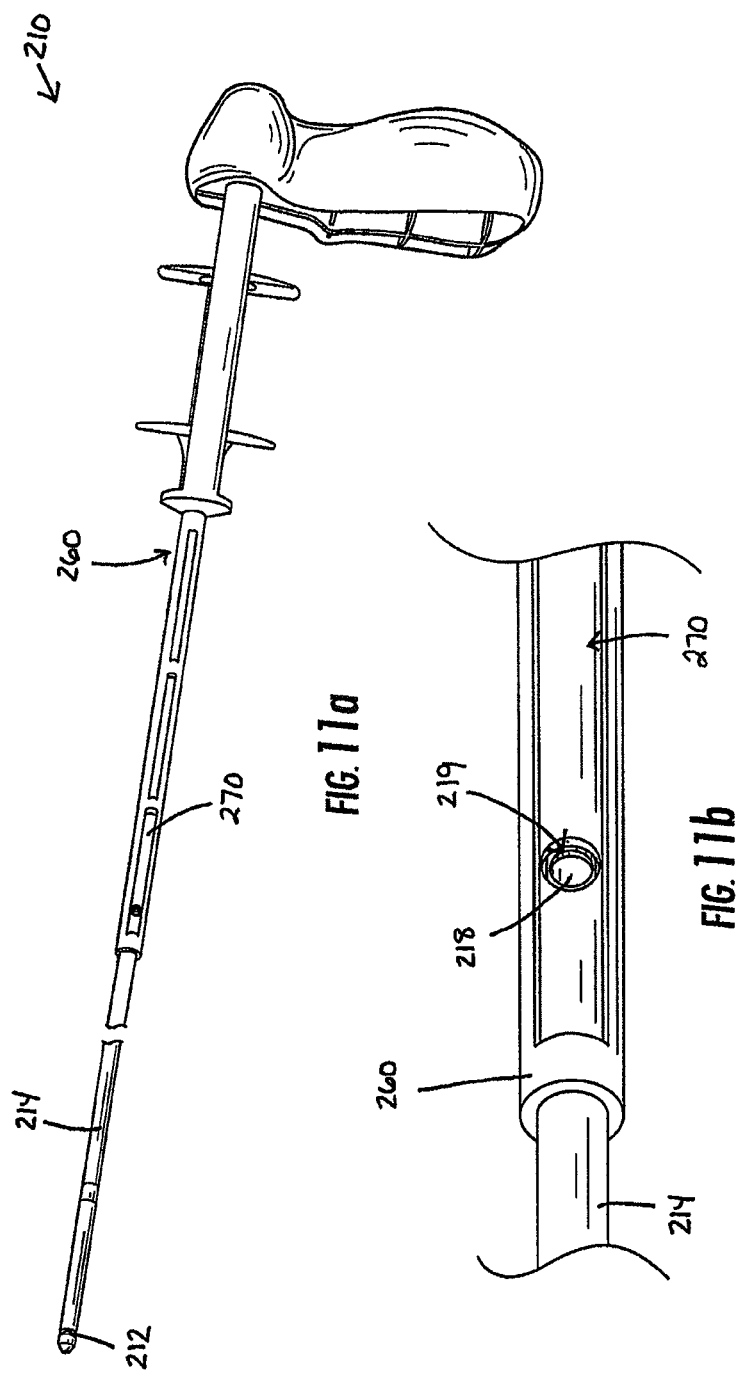
Figure 12:
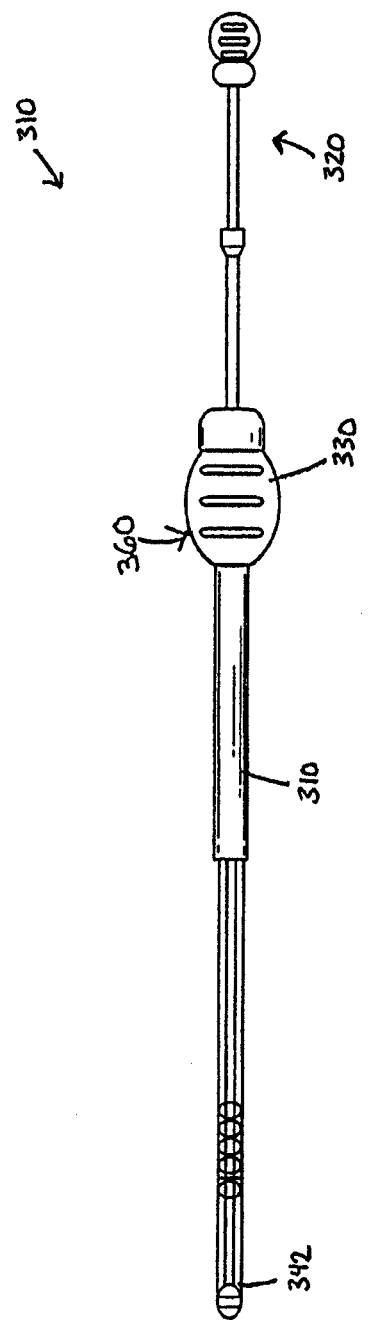

Having thus described the invention in general terms, reference will now be made to the accompanying drawings, which are not necessarily drawn to scale, and wherein:

FIG. 1 is a perspective view of a delivery device in a hold position according to an embodiment of the present invention;

FIG. 2 is a top view of the delivery device of FIG. 1;

FIG. 3 is a side view of the delivery device of FIG. 1;

FIG. 4 is a perspective view of the delivery device of FIG. 1 in an intermediate position;

FIG. 5 is a top view of the delivery device of FIG. 4;

FIG. 6 is a side view of the delivery device of FIG. 4;

FIG. 7 is a perspective view of the delivery device of FIG. 1 in a release position;

FIG. 8 is a top view of the delivery device of FIG. 7;

FIG. 9 is a side view of the delivery device of FIG. 7;

FIG. 10 is a perspective view of a delivery device according to another embodiment of the present invention;

FIG. 11a is a perspective view of a delivery device according to yet another embodiment of the present invention;

FIG. 11b is an enlarged portion of the delivery device of FIG. 11a;

FIG. 12 is a perspective view of a delivery device according to another embodiment of the present invention; and FIG. 13 is an illustration of a delivery device being inserted into an endoscope in accordance with an embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a delivery device 10 capable of being deployed within a lumen proximate to a target area. "Target area," as used herein, is not meant to be limiting, as the target area, could be a stricture, lesion, tumor, occlusion, fistulae, or other complication where the lumen passageway has been significantly reduced.

The delivery device 10 is typically utilized to deploy an implantable device (not illustrated) within a lumen. However, the delivery device 10 is also capable of being used for surgical or endoscopic techniques to decrease the complexity of the procedure. For example, the delivery device 10 is also applicable to laparoscopy and arthrectomy.

It is understood that the delivery device 10 is applicable to a wide range of intraluminal applications. For example, the delivery device 10 could be used for implanting an implantable device within lumina of the esophagus, trachea, arteries, or the biliary tract. The implantable device could be, for example, a stent, drug delivery device, or other medical device or drug known to those skilled in the art. Furthermore, any number of configurations of implantable devices could be incorporated and still be within the present scope of the invention. An exemplary embodiment of the interstice geometry of a stent and methods of manufacturing the stent is disclosed in U.S. Patent Publication No. 20040127973, entitled "Removable Biliary Stent," which is assigned to the assignee of the present application and is incorporated herein by reference.

With reference to FIGS. 1 through 9, a delivery device 10 according to an embodiment of the present invention is shown. The delivery device 10 may include an inner tubular member 12, an outer tubular member 14, a handle 30, and a deployment mechanism 20. In general, the inner tubular member and the outer tubular member have at least two positions. As illustrated in FIGS. 1 and 3, in a first position, the tubular members 12, 14 are configured to hold or contain at least a portion of the implantable device. And, as illustrated in FIGS. 7 and 9, in a second position, the tubular members 12, 14 are configured to release the implantable device. For example, in the first position, the implantable device may be configured to fit into the distal end of the outer tubular member. And in the second position, the implantable device is released by the outer tubular member either by the inner tubular member holding the implantable device in place as the outer tubular member is slid away or by the inner tubular member pushing the implantable device out of the outer tubular member as the inner tubular member is slid toward or further away from the distal end of the outer tubular member or a combination thereof. The handle 30 and deployment mechanism 20 are adapted to allow an operator, such as a physician, to hold and operate the delivery device 10, including moving the tubular members 12, 14 between the first and second positions.

In particular, either the inner tubular member 12 or outer tubular member 14 extends from the handle 30. Each of the tubular members 12, 14 extends from a proximal end 36, 40 to a distal end 38, 42 relative to the handle 30. The inner tubular member 12 is positioned within an outer tubular member 14 and at least one of the tubular members 12, 14 is slidable relative to the other tubular member 12, 14. For example and according to the illustrated embodiments, the inner tubular member 12 extends from the handle 30 and the outer tubular member 14 is slidable along and around the inner tubular member 12. However, it is understood that according to other embodiments of the present invention the inner tubular member may be slidable along and in the outer tubular member or yet in other embodiments both the inner tubular member and outer tubular member may both be slidable relative to each other.

Both the inner tubular member 12 and outer tubular member 14 are typically flexible for positioning and maneuvering the tubular members within a lumen. Each of the inner 12 and outer 14 tubular members are also typically transparent or semi-transparent, such that the inner tubular member is visible through the outer tubular member. Moreover, the inner tubular member 12 may include markers for positioning and deploying the implantable device, although the inner and/or outer tubular members could include markers if desired. For instance, the distal end of the outer tubular member 14 may include a marker to locate the distal end of the implantable device. The inner tubular member 12 is slightly smaller in diameter than the outer tubular member 14 such that the inner tubular member may slide within the outer tubular member.

However, the inner 12 and outer 14 tubular members may be various sizes and configurations to accommodate a desired implantable device. For example, the inner 12 and outer 14 tubular members could be about 6 to 10 mm in diameter and about 250-500 mm in length. Each of the inner 12 and outer 14 tubular members could also be various diameters and wall thicknesses along the length of each tubular member for varying flexibility and/or aiding in securing or deploying the implantable device. For example, the outer tubular member 14 could have an incrementally larger diameter from near its respective side opening to the distal opening 18, and could also have a greater wall thickness proximate to the side opening 18.

A substantial portion of each of the inner 12 and outer tubular members 14 may include an assembly of polymeric materials and a metal coil (not illustrated). For instance, the polymeric materials could be a polytetrafluoroethylene ("PTFE"), such as Teflon® (E.I. DuPont de Nemours and Co. Corp.), and a polyether block amide ("PEBA"), such as Pebax® (Atofina Corp.). Generally, a PTFE liner is placed over a mandrel, and a coil is wound around the PTFE liner while positioned on the mandrel. The PEBA material is configured as a tubular member and slid over the wound coil and the PTFE liner while the assembly is supported on the mandrel. The assembly is then heated such that the PEBA outer sleeve and the PTFE liner are adhered together over the coil to form a tubular member assembly. The PTFE liner is typically etched so that the PEBA material attaches or fuses to the PTFE material. During the etching process, the PTFE liner is discolored from a clear color to a yellowish brown. Because the PTFE liner is slightly discolored, the side opening provides greater visibility where an optical instrument would be unable to clearly view through the liner itself. The remaining portions of the inner 12 and outer 14 tubular members (i.e., the distal portions of the tubular members where no coil is present) are typically a combination of PTFE and PEBA materials. The interior of the inner 12 and outer 14 tubular members, in one embodiment, are a low-friction PTFE material, which allows various devices and instruments to slide therethrough and requires lower deployment forces when retracting the outer tubular member 14 during deployment of the implantable device. The inner tubular member 12 may be fixedly attached at its proximal end adjacent to the handle 30. Thus, the proximal end of the inner tubular member 12 may be molded or otherwise attached to a portion of the handle 30, such as with an adhesive.

The coil may extend from the proximal end of the each of the inner 12 and outer 14 tubular members and within each of the inner and outer tubular members proximate to a respective side opening 18. In particular, each coil may be positioned proximal of a respective side opening. The coils maintain a desired flexibility for the inner 12 and outer 14 tubular members, but also preventing kinking or buckling when manipulating the inner and outer tubular members within the lumen.

The inner tubular member 12 may further include a pusher 26 that is configured to engage the implantable device by pushing the implantable device out of the distal end of the outer tubular member when the inner tubular member is moving toward the distal end of the outer tubular member. Another example and according to the illustrated embodiment, the inner tubular member 12 may have a pusher 26 that is configured to hold the implantable device in place as the outer tubular member 14 moves away from the distal end of the inner tubular member 38.

The implantable device is deployed within a lumen and proximate to a target area using techniques known to those skilled in the art. For instance, the implantable device may be introduced orally with the delivery device 10, through the lumen, and proximate to a target area. The implantable device is typically contracted to a smaller first diameter from a relaxed position. Once contracted, the implantable device is positioned within the outer tubular member 14 of the delivery device proximate to the distal end of the outer tubular member. The inner tubular member 12 is positioned within the outer tubular member 14 such that the distal end of the inner tubular member is positioned proximate to the proximal end of the implantable device. Or at least a portion of the implantable device 16 may be positioned on the distal end of the inner tubular member 12 to engage the pusher 26.

It is understood that the pusher 26 shown and described above is only one embodiment of the present invention. For instance, the pusher 26 could be integrally formed with the inner tubular member 12 such that pusher is not a separate component of the inner tubular member. It is noted that although the term "pusher" is used herein, the pusher 26 does not always push the implantable device 16. The inner tubular member 12 and pusher 26 may remain stationary while the outer tubular member 14 is retracted. However, the pusher 26 may be configured to advance the implantable device 16 such that the inner tubular member 12 may be moved distally while the outer tubular member 14 remains stationary or is moved concurrently in a proximal direction As shown in the illustrated embodiment of FIGS. 1 through 9, the handle 30 may extend generally perpendicular from the length of the tubular members, similar to a "pistol grip." Other exemplary embodiments of the handle 130, 330 are illustrated in FIGS. 10 and 12. The handle may be made from a variety of materials. For example, the handle may be made from a polypropylene, a poly-vinyl chloride, or a high density polyethylene.

The deployment mechanism 20 may include one or more actuators 22 coupled to the outer tubular member 14. Depending on the length of the implantable device, there could be one actuator 22 for shorter implantable devices (e.g., 20-60 mm) (not illustrated) and two or more actuators for longer implantable devices (e.g., 80 mm), as shown in FIG. 1 through 9.

When utilizing two or more actuators 22, 23, the actuators may be operatively connected such that the actuators cooperate to deploy the implantable device. As shown in the illustrated embodiment of FIGS. 1 through 9 of the present invention, the deployment mechanism 20 may include a proximal actuator 23 and a distal actuator 22. The distal actuator 22 includes a base portion 44 that is slidable along the inner tubular member 12 and is affixed to the outer tubular member 14 such that the movement of the distal actuator 22 moves the outer tubular member 14 along the inner tubular member 12. The distal actuator 22 may include one or more flanges 46 that extend generally from the base portion 44 in a generally perpendicular direction from the tubular members 12, 14 for providing a surface for an operator's fingers to grab.

The proximal actuator 23 is operatively connected to the distal actuator 22. More specifically, the proximal actuator 23 may include a base portion 48 that is slidable along the inner tubular member 12 and one or more flanges 50 similar to the flanges 46 of the distal actuator 22. The proximal actuator 23 may further include two or more connector arms 52. Each arm 52 extends from the base portion 48 of the proximal actuator 23 in a direction generally parallel to the direction of the tubular members 12, 14 to a distal end 54 of the connector arms. The distal ends 54 of the connector arms extend distally beyond the base portion of the distal actuator 22 such that the distal actuator 22 is between the distal ends 54 of the connector arms and the base portion 48 of the proximal actuator. The connector arms 52 define an aperture 56 that extends from the distal end 54 of the connector arms to the base portion 48 of the proximal actuator. The distal actuator 22 is slidable within the aperture 56 independently from the proximal actuator 23. And the distal ends 54 of the connector arms and the base portion 48 of the proximal actuator inhibit the distal actuator 22 from escaping or moving beyond the aperture 56. Although the connector arms are described as being an integral portion of the proximal actuator, it is understood that the connector arms and the proximal actuator may be separate components that are attached to each other. For example, the connector arms may be attached to the base portion of the proximal actuator by one or more fasteners or by an adhesive. The actuators and the connector arms may be made from a variety of materials. For example, the actuators and the connector arms may be made from a polypropylene, a poly-vinyl chloride, or a high density polyethylene.

As shown in FIGS. 1 through 3, the outer tubular member 14 may be placed in an extended first position relative to the inner tubular member 12. In the extended first position, the proximal actuator 23 may be positioned generally as far from the handle 30 as possible while still allowing an operator to grab the flanges of the proximal actuator 23 with his or her fingers while palming the handle 30. In the extended first position, the distal actuator 22 is adjacent the distal ends 54 of the connector arms.

This arrangement of actuators 22, 23 allows users of the delivery device 10 to deploy the implantable device 16 with one hand if desired. For example, an operator may palm the handle 30 of the delivery device 10 with one of his or her hands and extend his or her fingers of the same hand to pull proximally on the proximal actuator 22, 23. The distal ends 54 of the connector arms would also pull the distal actuator 22 back with the proximal actuator 23. As the distal actuator 22 moves closer to the handle 30, the operator may extend his or her finder to pull directly on the distal actuator 22 rather than the proximal actuator 23. The aperture 56 defined by the connector arms 52 allows the distal actuator 22, and thus the outer tubular member 14 to move proximally toward the handle 30 even after the proximally actuator 23 abuts the handle 30 (as shown in FIGS. 4-6) until the distal actuator 22 abuts the proximal actuator 23 (as shown in FIGS. 7-9). The two actuators abutting each other and the handle 30 may be considered the second position, as described above, which is configured to release the implantable device from the distal end of the outer tubular member. In some applications, depending on the length of the implantable device, the implantable device may be released from the outer tubular member before the distal actuator abuts the proximal actuator.

The deployment mechanism 20 as described above is an example according to an embodiment of the present invention. However, the deployment mechanism 20 could be range of devices or actuators capable of deploying the implantable device 16 distally out of the outer tubular member 14. For example, the actuators 22 could be configured to slide the inner tubular member 12 distally within the outer tubular member 14 such that the outer tubular member remains stationary relative to the inner tubular member. Also, although the actuators 22 are T-shaped, the actuators could be configured as a trigger to grip the actuator. One or more of the actuators of the deployment mechanism 320 may be opposite the handle 330 from the distal ends of the tubular members as illustrated in FIG. 12.

The delivery device 10 further includes a protective member 60. Although the handle 30 and the actuators 22, 23 may be configured for operation with one hand, a user may tend to use his or her other hand to grab the outer tubular member 14 during deployment. The second hand may pinch down on the outer tubular member 14 which may adversely affect the ability for the inner and outer tubular members 12, 14 to slide relative to each other and thus affect the deployment accuracy of the delivery device 10. Also, due to the tortuous path often followed by tubular members 12, 14 within the patient's lumen or from another device, such as an endoscope, the tubular members 12, 14 may become pinched or otherwise interfered with such that the ability of the inner and outer tubular members 12, 14 to slide relative to each other may be compromised. In general, the protective member 60 provides a degree of insulation to at least a portion of the outer tubular member 14 from external forces, such as an operator's hand. Insulating a portion of the outer tubular member 14 from external forces reduces the likelihood of the outer tubular member 14 being pinched and interfering with the movement between the inner and outer tubular members 12, 14.

The shape and size of the protective member 60 may vary. For example, the protective member 60 may extend from the handle 30 beyond the actuators 22, 23 and toward the distal end 42 of the outer tubular member. The length of the protective member 60, i.e. the extent of which the protective member 60 extends toward the distal end 42 of the outer tubular member, may vary. In general, the protective member 60 in one embodiment is long enough to extend beyond the actuators 22, 23. This provides a large enough area for a user to grab with his or her hand. However, the protective member 60 is not extended so far in this embodiment as to significantly interfere with the distal ends 38, 42 of the inner and outer tubular members and the deployment of the implantable device.

According to the embodiment of the present invention illustrated in FIGS. 1 through 9, the protective member 60 generally has a proximal region 62 and a distal region 64. The proximal region 62 extends distally from the handle 30 to the distal region 64. The proximal region 64 is configured to extend around the actuators 22, 23, including the connector arms 52. For example and as illustrated, the proximal region 64 may include two extension arms 66 that are dimensioned to extend along and on the outside of the connector arms 52. The two extension arms 66 also define two grooves 68 for the flanges 46, 50 of the actuators to extend through and slide within. The length of the proximal region 64, including the grooves 68 is long enough to accommodate the full expected operational range of the actuators 22, 23. In other words, the grooves 68 are long enough to accommodate the extended first position described above. The number of the grooves may vary according to the number of flanges of the actuators, including an embodiment of just one groove. According to the illustrated embodiment, the proximal region is coupled to the handle. However, in other embodiments, the proximal region, and thus the protective member, may be free to slide along the outer tubular member.

The distal region 64 extends from the proximal region 62 toward the distal end 42 of the outer tubular member. The distal region 64 provides a surface or an area that insulates the outer tubular member 14 from external contact. The length of the distal region 64 may vary. For example, the distal region 64 may be approximately 10-15 cm in length, which is large enough area for a hand to grab or may be approximately or may be approximately 50-60 cm depending on the length of the inner and outer tubular members 12, 14. As illustrated, the distal region 64 may be a sheath that envelopes at least a portion of the outer tubular member 14. Moreover, the distal region 64 is adapted to absorb at least some or all of an impact or pressure from a user grapping or grasping the distal region 64 with his or her hand or from the walls of the patient's lumen. In other words, the distal region 64 reduces the likelihood of the outer tubular member 14 being pinched when the user grabs the delivery device 10 outside of the handle 30 or deployment mechanism 20 or being pinched or by the walls of the patient's lumen. The distal region 64 may be relatively rigid for absorbing and resisting the impact rather than deforming and potentially pinching the outer tubular member 14. The distal region 64, as well as the proximal region 62, may be made from a variety of materials including, but not limited to, high density polypropylene or high density polyethylene or polyetheretherketone (PEEK). The material or coating of the protective member 60 may be configured to have a low friction coefficient to facilitate the movement between the protective member 60 and the outer tubular member 14 or between the protective member 60 and the walls of the patient's lumen.

Although the distal region 64 is illustrated in FIGS. 1 through 9 as a sheath having a solid tubular wall surrounding the outer tubular member, the distal region 64 may vary. For example, instead of a solid tubular wall, the distal region may define a number of grooves and apertures or include a number of parallel arms extending along a portion of the outer tubular member and connected by a series of rings along and around the outer tubular member to form a cage-like structure.

For example, in the embodiment of the present invention illustrated in FIGS. 11a and 11b, the protective member 260 of the delivery device 210 includes a distal region 264 that defines at least one groove 270 corresponding to side openings 218, 219 defined in each of the inner 212 and outer 214 tubular members. Each of the side openings 218, 219 and at least one of grooves 270 of the distal region may be capable of aligning with one another such that an optical device (not illustrated) may view a target area within a lumen. Therefore the side openings 218, 219 and the groove 270 of the distal region may provide increased visibility of the target area. Grooves defined within the distal region may also be used to allow the operator to view markers on one or both of the inner and outer tubular members.

Moreover, the structure of the proximal region may vary as well. For example, according to some embodiments of the present invention, the deployment mechanism may be opposite the handle from the distal ends of the outer tubular member and the inner tubular member, as shown in FIG. 12. In such embodiments, the protective member 360 of the delivery device 310 may extend from the handle 330 toward the distal end 342 of the outer tubular member without separate proximal and distal regions.

Also, in other embodiments, the protective member may not include a proximal region and may extend from the deployment mechanism. For example, according to another embodiment illustrated in FIG. 10, the protective member 160 may extend opposite of the deployment mechanism 120 from the handle 130 and toward the distal end 142 of the outer tubular member. The protective member 160 may be configured to slide along the outer tubular member 114. The protective member 160 may be contained between stops 172, 173 affixed along the outer tubular member 114 as shown such that the protective member 160 may be held in place by an operator as the outer tubular member 114 and the inner tubular member 112 are moving relative to each other.

Although the delivery device has been illustrated and described primarily as having an outer tubular member and an inner tubular member, other embodiments of the delivery device include various other elongate members configured to move relative to each other and retain and release an implantable device. Other examples may include, but are not limited to, inner and outer elongate members having complementary cross-sections and elongate members positioned side by side each other, such as opposing C-shaped members that are moveable to each other and configured to retain and release an implantable device.

The present invention includes several advantages. For instance, the protective member insulates at least a portion of the outer tubular member from the tendency of some operators to grab the outer tubular member while operating the delivery device. The protective member may also insulate at least a portion of the outer tubular member from the walls of the patient's lumen and reduce the likelihood of the inner and outer tubular members from be pinched due to the tortuous path the tubular members may have to follow in the patient's lumen. In some instances and embodiments, as shown in FIG. 13, the delivery device 510 may be delivered to the patient's lumen through the working channel of an endoscope 512. More specifically, the distal ends of the tubular members with the implantable device are inserted through an entry port 514 of the endoscope along the working channel (not visible in FIG. 13) of the endoscope and out of the distal end of the endoscope into the patient's lumen (not illustrated). The protective member 516 may be grabbed (as illustrated in FIG. 13) at the entry port 514 of the endoscope 512 by the operator and thus immobilizing the protective member 516 and the rest of the delivery device during deployment of the implantable device except for the outer tubular member, which is moveable through the handles, which helps the operator to achieve a high placement accuracy of the implantable device in the patient's lumen. In other words, the protective member reduces the likelihood of the outer tubular member being pinched or otherwise impinged by the operator or another external source and adversely affecting the deployment of the implantable device.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A delivery device for positioning and deploying an implantable device within a lumen, said delivery device comprising:
 a first elongate member having a proximal end with a longitudinal axis extending to a distal end;
 a second elongate member having a proximal end and a distal end, said first and second elongate members configured to cooperatively retain the implantable device near the distal ends and to move relative to each other to release the implantable device into the lumen, wherein the first elongate member includes an outer tubular member and the second elongate member includes an inner tubular member extending slidably within the outer tubular member, and wherein a space is defined between the inner tubular member and the outer tubular member near the distal ends to retain the implantable device;

a handle coupled to the proximal end of at least one of the first and second elongate members;

a deployment mechanism coupled to at least one of the inner and outer tubular members and operable to cause a relative motion of the first and second elongate members, wherein the deployment mechanism comprises a first slidable actuator positioned proximal to a second slidable actuator and operably connected thereto, such that slidably retracting the first slidable actuator moves the second slidable actuator and the outer tubular member proximally and longitudinally relative to the inner tubular member, and wherein one of the actuators is coupled to the proximal end of the outer tubular member; and a protective member in engagement with the handle and configured to extend from the handle around and beyond the deployment mechanism and over at least one portion of the elongate members wherein relative movement occurs, said protective member configured to inhibit impingement of external forces on the relative movement of the elongate members from the handle around and beyond the deployment mechanism and over at least one portion of the elongate members, wherein the protective member extends from the handle and over the deployment mechanism toward the distal end of the outer tubular member, such that a distal end of the protective member terminates proximal to the distal end of the outer tubular member;

wherein at least a portion of the second elongate member is disposed within the first elongate member, such that at least a portion of the second elongate member is longitudinally and axially displaceable relative to the first elongate member; and wherein the first actuator has a first flange extending transverse to the longitudinal axis and greater than a diameter of the protective member, and the second actuator has a second flange extending transverse to the longitudinal axis and greater than the diameter of the protective member.

2. A delivery device of claim 1, wherein the protective member includes a protective tubular member extending over a proximal portion of the inner and outer tubular members, the protective tubular member configured to inhibit impingement of external forces caused by a grip of an operator.

3. A delivery device of claim 1, wherein the protective member includes a proximal region and a distal region extending from the handle to distally beyond the deployment mechanism and toward the distal end of the outer tubular member, and wherein the proximal region defines one to a plurality of grooves in which the flanges of the actuators are slidable within and the distal region extends along and around at least a portion of the outer tubular member.

4. A delivery device of claim 3, wherein the distal region includes a substantially solid tubular wall.

5. A delivery device of claim 3, wherein the distal region defines at least one aperture.

6. A delivery device of claim 1, wherein the protective member is formed substantially from a material selected from the group consisting of a polypropylene, a poly-vinyl chloride, and a polyethylene.

7. A delivery device for positioning and deploying an implantable device within a lumen comprising:

an outer tubular member with a longitudinal axis extending to a distal end, and an inner tubular member positioned within the outer tubular member such that the inner tubular member and outer tubular member are movable relative to each other between at least a first position and a second position, wherein in the first position the outer and inner tubular members are configured to hold the implantable device and in the second position the outer and inner tubular members are configured to release the implantable device;

a handle coupled to at least one of the outer tubular member and the inner tubular member;

a deployment mechanism coupled to at least one of the inner and outer tubular members and operable to deploy the implantable device within the lumen; wherein the handle and the deployment mechanism are adapted to be operated by a first hand of an operator for moving the outer and inner tubular members between the at least first and second positions wherein the deployment mechanism comprises a first slidable actuator positioned proximal to a second slidable actuator and operably connected thereto, such that slidably retracting the first slidable actuator moves the second slidable actuator and the outer tubular member proximally and longitudinally relative to the inner tubular member; and a protective member in engagement with the handle and extending along at least a portion of the outer tubular member from the handle around and beyond the deployment mechanism toward a distal end of the outer tubular member, wherein the protective member extends from the handle and over the deployment mechanism toward the distal end of the outer tubular member, such that a distal end of the protective member terminates proximal to the distal end of the outer tubular member;

wherein the protective member is adapted to be grasped by a second hand of the operator independently from the moving of the outer and inner tubular members between the at least first and second positions; wherein the first actuator has a first flange extending transverse to the longitudinal axis and greater than a diameter of the protective member, and the second actuator has a second flange extending transverse to the longitudinal axis and greater than the diameter of the protective member.

8. A delivery device of claim 7, wherein the protective member includes a distal region defining a sheath that envelopes at least a portion of the outer tubular member and wherein the outer tubular member is slidable within the sheath.

9. A delivery device of claim 8, wherein the deployment mechanism is positioned between the handle and the distal end of the outer tubular member and wherein the protective member includes a proximal region that extends distally from the handle and beyond the deployment mechanism to the distal region.

10. A delivery device of claim 9, wherein the proximal region of the protective member defines one to a plurality grooves in which the first and second flanges extend through and are slidable within.

11. A delivery device of claim 10, first actuator is coupled to a proximal end of the inner tubular member and the second actuator is positioned between the handle and the first actuator and includes one to a plurality of connector arms for operatively coupling the first and second actuators together; and wherein the proximal region of the protective member includes one to a plurality of extension arms that extend along the outside of the connector arms.

12. A delivery device of claim 11, wherein each actuator includes two flanges, and both of the connector arms of the second actuator and the extension arms of the proximal region of the protective member define two grooves in which the flanges extend through and are slidable within.

13. A delivery device for positioning and deploying an implantable device within a lumen comprising:
- an outer tubular member having a longitudinal axis extending from a proximal to a distal end, wherein the implantable device is positioned proximate to the distal end of the outer tubular member;
- an inner tubular member positioned within the outer tubular member and having proximal and distal ends, wherein the outer tubular member is capable of sliding over the inner tubular member between at least a first position and a second position;
- a handle coupled to the proximal end of the inner tubular member;
- a deployment mechanism operable to slide the outer tubular member between the first and second positions, wherein the deployment mechanism has one to a plurality of actuators, including a first slidable actuator coupled to the proximal end of the outer tubular member positioned proximal to a second slidable actuator and operably connected thereto, such that slidably retracting the first slidable actuator moves the second slidable actuator and the outer tubular member proximally and longitudinally relative to the inner tubular member;
- and a protective member in engagement with the handle and extending from the handle around and beyond the deployment mechanism toward the distal end of the outer tubular member to provide insulation to at least a portion of the outer tubular member extending beyond the deployment mechanism, wherein the protective member extends from the handle and over the deployment mechanism toward the distal end of the outer tubular member, such that a distal end of the protective member terminates proximal to the distal end of the outer tubular member; wherein the first actuator has a first flange extending transverse to the longitudinal axis and greater than a diameter of the protective member, and the second actuator has a second flange extending transverse to the longitudinal axis and greater than the diameter of the protective member.

14. A delivery device of claim 13, wherein the protective member is coupled to the handle.

15. A delivery device of claim 13, the protective member includes a proximal region defining one to a plurality of grooves in which the flanges extend through and slide within.

16. A delivery device of claim 15, wherein the second actuator is between the first actuator and the handle, the second actuator includes at least two connector arms for operatively coupling the second actuator to the first actuator and wherein the proximal region of the protective member includes at least two extension arms that extend along and on the outside the connector arms.

17. A delivery device of claim 13, wherein the protective member includes a distal region extending distally beyond the deployment mechanism in both the first and second positions toward the distal end of the outer tubular member and defining a sheath that envelopes at least a portion of the outer tubular member and wherein the outer tubular member is slidable within the sheath.

18. A delivery device of claim 17, wherein the sheath includes a substantially solid tubular wall.

19. A delivery device of claim 17, wherein the sheath defines at least one aperture.

* * * * *